United States Patent
Gonzalez et al.

(10) Patent No.: US 7,122,150 B2
(45) Date of Patent: Oct. 17, 2006

(54) ELECTRONIC READER FOR STERILIZATION MONITORS

(75) Inventors: Bernard A. Gonzalez, St. Paul, MN (US); Rodney K. Hehenberger, Apple Valley, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 295 days.

(21) Appl. No.: 10/044,441

(22) Filed: Jan. 11, 2002

(65) Prior Publication Data

US 2003/0133830 A1   Jul. 17, 2003

(51) Int. Cl.
*A61L 2/00* (2006.01)

(52) U.S. Cl. .............. 422/28; 422/3; 422/105; 422/119; 21/2

(58) Field of Classification Search ........... 422/119, 422/3, 105, 82.05, 56, 28; 21/2
See application file for complete search history.

(56) References Cited

U.S. PATENT DOCUMENTS

| | | | |
|---|---|---|---|
| 3,982,893 A * | 9/1976 | Joslyn | 436/6 |
| 4,850,716 A | 7/1989 | Baker et al. | 374/160 |
| 5,565,634 A | 10/1996 | Graessle et al. | 73/865.9 |
| 5,745,039 A | 4/1998 | Hof et al. | 340/590 |
| 6,063,631 A | 5/2000 | Ignacio | 436/1 |
| 6,166,538 A | 12/2000 | D'Alfonso | 324/228 |
| 6,318,151 B1 * | 11/2001 | Wang et al. | 73/25.01 |
| 6,488,890 B1 * | 12/2002 | Kirckof | 422/56 |

FOREIGN PATENT DOCUMENTS

| WO | WO 98/33286 | 7/1998 |
|---|---|---|
| WO | WO 01/10476 | 2/2001 |

* cited by examiner

*Primary Examiner*—John Kim
*Assistant Examiner*—Brad Y. Chin
(74) *Attorney, Agent, or Firm*—Daniel R. Pastirik

(57) ABSTRACT

A system for determining the efficacy of a sterilization process and communicating that determination to a remote device. The system includes a sterilization sensor and a reader adapted to receive that sterilization sensor. The sterilization sensor has an indicator that undergoes a predetermined optical change when exposed to a sterilization process. The reader has an illumination source for illuminating the sterilization sensor, a color sensor for evaluating the condition of the illuminated sterilization sensor, and an interpretation circuit for interpreting the output of the color sensor to determine whether the optical change has taken place. The reader also has a communication circuit for communicating data from the interpretation circuit to the remote device. In the preferred embodiments, the sterilization sensor is disposable and the reader is reusable.

7 Claims, 2 Drawing Sheets

ELECTRONIC READER FOR STERILIZATION MONITORS

TECHNICAL FIELD

The present invention is directed to sterilization monitors. In particular the invention relates to a sterilization monitor in which a change in the monitor resulting from an exposure to a sterilization cycle is remotely detectable. The sterilization monitor can be read remotely without the need to open a package containing sterilized goods.

BACKGROUND OF THE INVENTION

A reliable supply of sterile instruments and supplies is important to modem medical practice. Various types of apparatus are known for sterilizing reusable goods within a hospital setting. Among the best known is the steam autoclave, which uses high temperature and high pressure steam to render medical goods sterile. When used as a sterilizing gas, steam is fast and effective, but its use requires high temperatures. Goods that cannot withstand autoclaving temperatures can be sterilized with sterilizers using biocidal gases such as ethylene oxide or hydrogen peroxide. Some types of medical goods are also suited to being sterilized by a liquid bath.

Whatever the selected method and sterilizing agent, an important part of the process of providing sterile goods is verifying that conditions necessary for sterilizing are met. Two broad classes of indicators are typically used for such verification. The first class, the so-called biological indicators, includes devices that employ viable spores of particularly hardy stains of bacteria. After a sterilizing cycle, the biological indicator is placed in an environment conducive to bacterial growth. If no growth occurs, an effective cycle is presumed. The second class is the so-called chemical indicators; these devices include a chemical compound that undergoes some sort of change (e.g., color, physical or chemical state, etc.) when subjected to a set of pre-determined conditions of sterilization within a sterilizing chamber. If the change occurs in the indicator, the sterilization cycle is presumed effective.

One change chemical indicators can undergo is a change in state. An indicator can, for example, melt. Devices that incorporate such an indicator can be made useful for remote monitoring such that the indicator can be assessed at a short distance without the need for its visual inspection. Melting of the indicating substance can, for instance, permit a physical rearrangement of a magnetostrictive element within the indicator which can be detected remotely by well-known electronic techniques.

Remote monitoring is an advantage because it is typical to enclose medical goods within a package or wrapping prior to sterilization. For example, the surgical instruments desired for a particular procedure can be laid out on a tray in a convenient layout and wrapped as an assembly in material that is porous to the sterilizing gas but nonporous to bacteria. The wrapped tray can be sterilized and maintained as a wrapped assembly until delivered to the surgical suite. Often a chemical indicator is attached to the outside of the wrapped assembly, and a change in the indicator to show that the exterior was subjected to sterilizing conditions is taken as a proxy showing that instruments in the interior of the wrapped assembly have also been rendered sterile. It may be preferred, however, to assess the sterilization of the goods by direct measurement of the conditions within the enclosed packaging material. While it is possible to include another chemical indicator within the wrapped assembly, unless adapted for remote monitoring its condition may not be reliably known until the tray is unwrapped in the surgical suite. At that point, it is inconvenient to learn that the goods are not sterile. It is particularly inconvenient if nonsterile goods from a newly unwrapped tray are placed inadvertently within the sterile field before being noticed; in such case the process of preparing the suite for surgery may have to begin again.

Known indicators adapted for remote monitoring generally have the disadvantage of being capable of only a single use, and mechanical components contained in such monitors are substantially more expensive than standard indicators.

SUMMARY OF THE INVENTION

In one aspect, the present invention provides systems for determining the efficacy of a sterilization process and communicating that determination to a remote location. The systems employ a sterilization sensor that comprises an indicator that undergoes an optical change when exposed to an efficacious sterilization process. The systems also use a reader that is adapted to receive the sterilization sensor. The reader generally comprises: (a) an illumination source for illuminating the sterilization sensor; (b) a first color sensor for evaluating the condition of the illuminated sterilization sensor; (c) an interpretation circuit for interpreting the output of the color sensor to determine whether the optical change has taken place; and (d) a communication circuit for communicating data from the interpretation circuit to the remote location.

In another aspect, the invention provides methods of determining the efficacy of a sterilization process. The methods generally comprise the following:

(a) providing a sterilization sensor comprising an indicator that undergoes a predetermined optical change when exposed to a sterilization process;
(b) placing the sterilization sensor within a reader;
(c) placing the reader with the sterilization sensor inside a package of goods;
(d) subjecting the package to sterilizing conditions; and
(e) interrogating the reader without opening the package to learn whether the optical change has taken place.

DETAILED DESCRIPTION OF PREFERRED EMBODIMENTS

Figure 1:
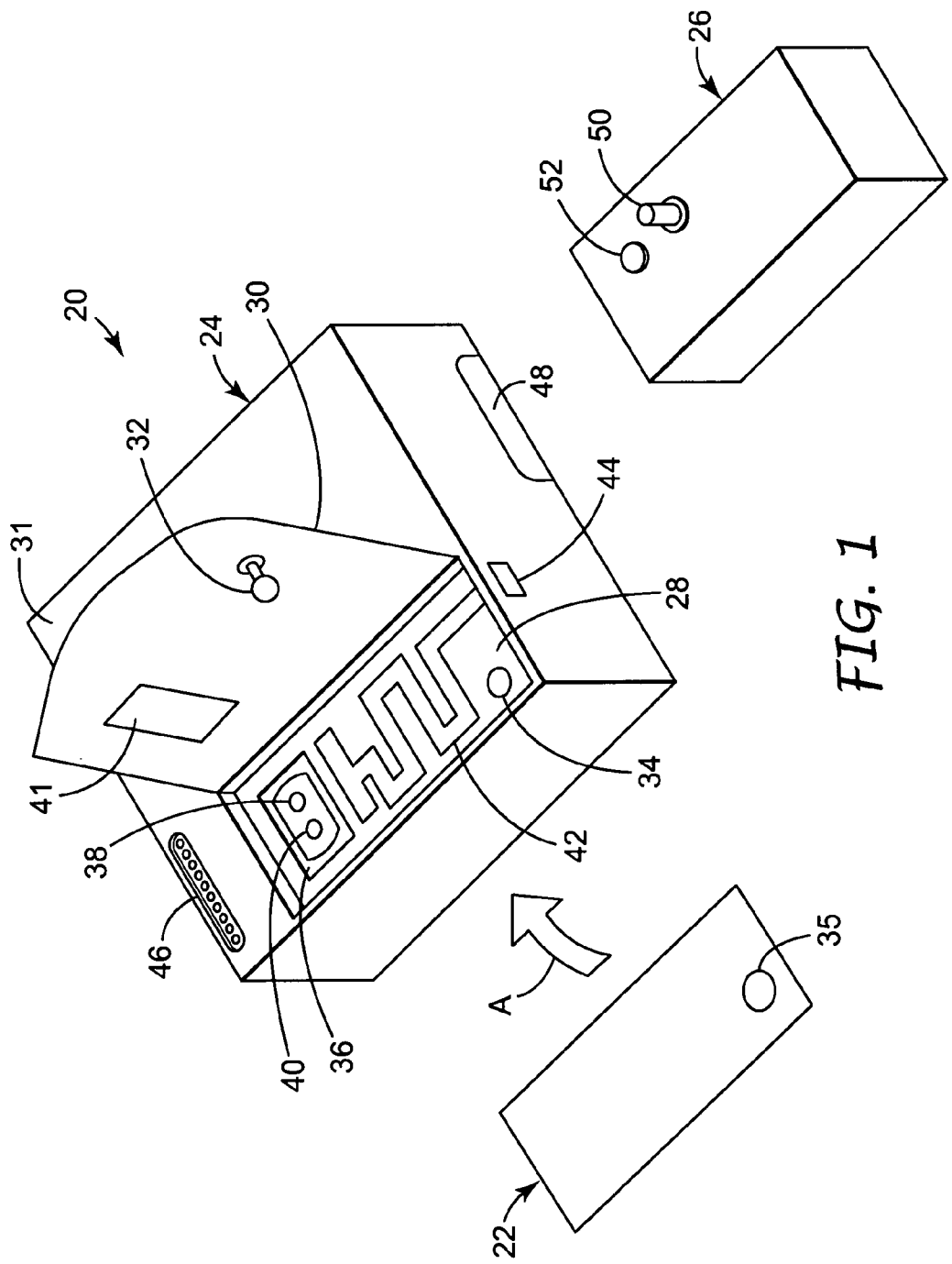
FIG. 1 is a perspective view of a system for determining the efficacy of a sterilization process according to the present invention.

The systems and methods of the invention generally provide the security of accurately assessing sterilizing conditions directly within a wrapped container or pack, the convenience of ascertaining that assessment before the pack reaches the surgical suite, and low cost to the medical consumer. Such advantages are accomplished by using an electronic reader adapted for inclusion within packs of goods to be sterilized and having chemical resistance capable of withstanding sterilizing conditions multiple times and through multiple uses. The reader will generally include a place to receive a disposable sterilization sensor that is capable of undergoing a visible change upon exposure to sterilizing conditions. In this way, the medical consumer is only charged directly for the inexpensive sterilization sensor, while the cost of the more expensive reader can be divided among many patients. The reader can also include a mechanism so that its assessment of the sterilization sensor can be discovered without opening the sterilized pack.

The present invention also includes a system for determining the efficacy of a sterilization process and communicating that determination to a remote device. The system generally includes a sterilization sensor and a reader adapted to receive that sterilization sensor. The sterilization sensor can have an indicator that undergoes a predetermined, or selected, optical change when exposed to a sterilization process. The reader generally has an illumination source for illuminating the sterilization sensor, a color sensor for evaluating the condition of the illuminated sterilization sensor, and an interpretation circuit for interpreting the output of the color sensor to determine whether the indicated optical change has taken place. The reader will also generally include a communication circuit for communicating data from the interpretation circuit to a remote location. In the context of this invention, remote need not imply great distance, but rather is used to denote separation. In preferred embodiments, the reader assembly will be separated from the remote location without direct physical connection. In some contemplated embodiments, the data is only transmitted a short distance, but it is transmitted through the closed, opaque packaging material around sterilized goods. It is also contemplated, however, that one or more readers could communicate over short distance with a repeater capable of communicating over a longer distance via radio, other electromagnetic radiation, telephone, internet or other similar manner.

In some preferred embodiments of the system, an interrogator is present for commanding the communication circuit to communicate its data. In preferred embodiments, this interrogator also functions through packaging material. It is also usually preferred that the sterilization sensor be disposable and that the reader be reusable, or capable of retaining operability after being exposed at least once to sterilizing conditions.

The invention also provides methods of determining the efficacy of the sterilization process using the above-described systems and system components.

Referring to FIG. 1, a perspective view of one suitable system 20 for determining the efficacy of a sterilization process is illustrated. The system 20 includes a sterilization sensor 22, a reader 24 and, optionally, an interrogator 26. The reader 24 conveniently includes a chamber 28 sized and shaped to receive sterilization indicator 22 as indicated by arrow "A". The reader 24 also has a cover 30 attached to a housing 31 for closing the chamber 28 after the sterilization sensor 22 has been inserted. In preferred embodiments the cover 30 has some mechanism for retaining it in a closed position over the chamber 28. In the depicted embodiment, the cover 30 has a stud 32 adapted to be received within clasp 34 on the bottom of chamber 28, though it will be clear to the ordinary artisan that many other expedients lend themselves to this purpose. The sterilization sensor 22 has a hole 35 to permit stud 32 to pass into clasp 34.

Within the chamber 28 is a window 36 protecting an illuminator 38 and a color sensor 40. An opaque reflector 41 may be positioned on the cover 30 to exclude unwanted ambient light and to maximize reflection from the sterilization sensor 22. The chamber 28 may also have a tortuous pathway 42 to bring sterilizing gas in a controlled manner from the outside via gas port 44. The tortuous pathway may also be configured on the cover 30 or directly on the sterilization sensor 22. One of the ways that the reader 24 could possibly communicate the condition of sterilization sensor 22 to a remote location is via sound. The depicted embodiment shows a grill 46 for passing sound from the reader 24 for this purpose.

Since it is contemplated that the reader 24 will usually be reusable, some embodiments will require replacement of the power source; battery hatch cover 48 is provided for this purpose. In embodiments having a battery hatch cover 48, it is particularly convenient that this cover be gas tight to prevent the sterilizing gas from damaging the battery. Other power sources besides batteries are considered to be within the scope of the invention. For example mechanically-wound generators are considered suitable. Other power sources that draw their energy from some aspect of the sterilizing environment, e.g., heat or pressure, are also potentially suitable for use with the present invention.

Protection of sensitive components of the reusable reader from damaging conditions is generally important. It is contemplated, therefore, that glass barriers sealed with epoxy may be necessary to isolate some of the electronics from sterilizing conditions. Another expedient, which may be particularly useful when the reader 24 is expected to endure higher temperature sterilizing cycles, is a temperature sensitive mechanical switch that prevents the electronics from being energized by the power source during the hottest portions of the cycle.

The interrogator 26 commands the reader to communicate its assessment of the sterilization sensor 22 when the operator requires it. A push button 50 is provided so the operator can give this command, and a visual indicator 52, such as an LED, is provided to provide feedback to the operator that the interrogator 26 has power and is acknowledging. While a push button is convenient in many circumstances, other expedients are possible. For example, the interrogator 26 might have a proximity detector sensitive to the presence of the reader 24 and send an interrogation command whenever it is brought within a predetermined distance of the reader. Alternatively, the interrogator 26 can be an entirely passive device, with the reader 24 having a proximity detector sensitive to the presence of the interrogator 26, and with the reader 24 providing its assessment on the mere approach of the interrogator 26. The interrogator 26 conveniently communicates its command by a short-range radio signal, although other expedients such as an audible signal are contemplated.

Figure 2:
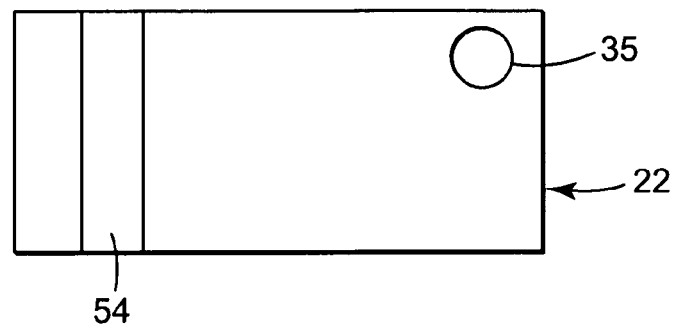
FIG. 2 is a front plan view of the sterilization sensor of FIG. 1.

Referring now to FIG. 2, a front plan view of sterilization sensor 22 is illustrated. The sterilization sensor 22 has an area containing an indicator substance 54. It should be noted that that the presence of hole 35 can be used to assure proper registration of the sterilization sensor 22 within the chamber 28, ensuring that the indicator substance 54 is properly positioned adjacent window 36. The indicating substance 54 undergoes a visible change when exposed to sterilizing conditions. The indicating substance 54 may also be arranged on sensor 22 such that it is visible to an observer without the need to remove the sensor from the reader 24. The art is aware of numerous chemical substances that can be used for the indicating substance, and the exact choice depends the sterilizing process or processes to be monitored. When a hydrogen peroxide vapor process is to be monitored, the use of acid fuchsin is considered particularly suitable, which compound evinces a strong color change from purple to colorless when exposed to sterilizing conditions, though other color change schemes (including a change from one color to another) may also be accomplished. Additional information on this compound and its use as an indicating substance suitable for use in connection with the present invention can be found in coassigned U.S. Pat. No. 6,063,631 (Ignacio), entitled "Sterilization Indicator," which is hereby incorporated by reference.

Figure 3:
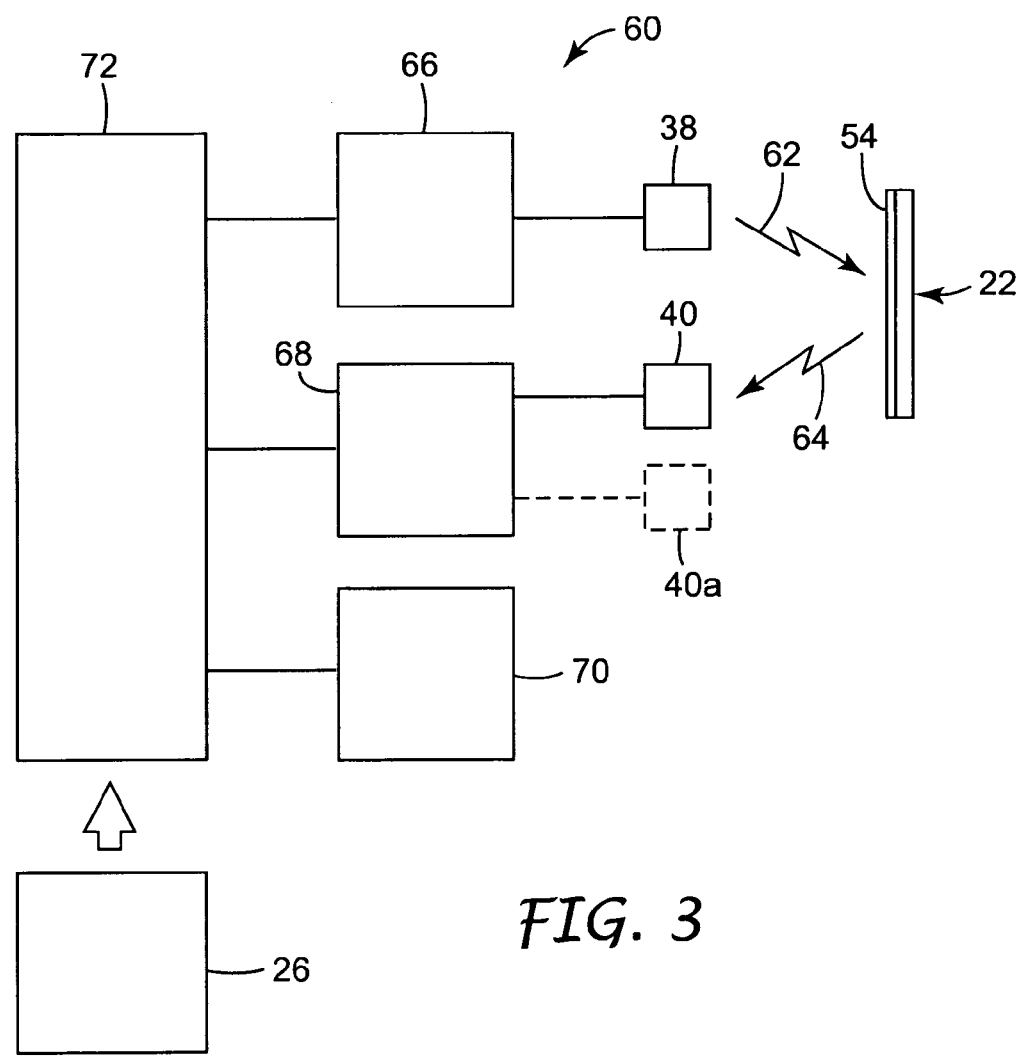
FIG. 3 is a block diagram of electronic circuitry for the system of FIG. 1.

A block diagram of electronic circuitry for the system 20 is illustrated in FIG. 3. The overall circuit 60 includes one or more illuminators 38 (only one is depicted in FIG. 3), which will supply radiant illumination 62 to the indicator substance 54. The light 64 reflected off indicator substance 54 is sensed by color sensor 40, the color sensor having been selected so that its output changes dramatically when the color of indicating substance 54 performs its optical change upon exposure to sterilizing conditions. This can be accomplished, for example, by an optical filter centered around the predominant frequency reflected off indicator substance 54 in one of its states, although other expedients will suggest themselves to the ordinary artisan. In most preferred embodiments, illumination source 38 is conveniently connected to an illumination control circuit 66, so the source is not always draining power.

Output from the color sensor 40 is directed to interpretation circuit 68, which interprets the output of color sensor 40 to arrive at a reportable sterile/nonsterile decision. It is contemplated that some embodiments will have a second, different color sensor 40a, which is also connected to the interpretation circuit 68. In these embodiments color sensor 40 and color sensor 40a are sensitive in opposite ways to the optical change in indicator substance 54 upon exposure to sterilizing conditions. Requiring agreement between these two sensors as to whether the optical change has occurred could promote a more reliable decision about sterility. In some embodiments, the interpretation circuit 68 is made from the minimum components in order to reduce cost. In other embodiments, enough processing power and memory is provided so that trends in the intensity of the light 64 that is reflected off indicator substance 54 can be tracked for the purpose of compensating for aging of the illuminator 38 or the color sensors 40 and/or 40a.

The decision of the interpretation circuit 68 is available to communication circuit 70. Communication circuit 70 is capable of transmitting at least the information about sterile/nonsterile to a remote location. This could be as simple as an audible signal generator capable of making two distinctly different sounds, one indicative of the sterile condition, the other indicative of the nonsterile condition. The invention also contemplates embodiments where additional information is transmitted to the remote location. For example, the systems and methods of the invention may be made part of an automated record system whereby information related to sterilization precedures (e.g., reader identity numbers, pack contents, type and conditions of sterilization processes, sterilization verification data, etc.) is fed to a database and there stored or collected with other information within the health care facility. The reader could also communicate information related to inventory by, for example, collecting and disseminateing self-identification information to a hospital's inventory control system to reconcile its stock of instruments with needed sterilization treatments. Such information can also be stored in digital memory such as a disk drive.

It will also be understood that output modes other than sound are contemplated by the invention. In particular, some embodiments can communicate sterile/nonsterile decision and other information via short-range radio communication. While frequencies between 300 and 500 MHz are among those considered suitable, other frequency ranges may be used for other advantage (such as an increased range), and the selection of any given frequency is considered well within the skill of the relevant art. Light and other portions of the electromagentic energy spectrum are also useful as modes of communication in the invention and, for any of those useful modes, antenae and resonators can be used to optimize the quality of the communication.

Some preferred embodiments of the overall circuit 60 will include an interrogation control circuit 72. When the operator uses the interrogator 26 to indicate that the assessment of the condition of indicator substance 54 is wanted, the interrogation control circuit 72 is activated. The interrogation control circuit 72 includes circuitry for recognizing the operator's request and activating the other circuits as needed so that the communication circuit 70 will respond to that request. The circuitry that recognizes the operator's request must, of course, be complementary to the circuitry of the interrogator 26 and able to react to the mode, e.g., audio or radio, that the interrogator uses.

We claim:

1. A system for determining the efficacy of a sterilization process and communicating that determination to a remote location, the system comprising:
   a sterilization sensor comprising an indicator that undergoes an optical change when exposed to an efficacious sterilization process;
   a reader adapted to receive the sterilization sensor, the reader comprising
   an illumination source for illuminating the sterilization sensor,
   a first color sensor for evaluating the condition of the illuminated sterilization sensor,
   an interpretation circuit for interpreting the output of the color sensor to determine whether the optical change has taken place,
   a communication circuit for communicating data from the interpretation circuit to the remote location; and
   the reader with the sterilization sensor therein and adapted for inclusion within packs of goods to be sterilized and capable of withstanding sterilizing conditions multiple times and through multiple uses.

2. The system according to claim 1 wherein the sterilization sensor is disposable and the reader is reusable.

3. The system according to claim 1 further comprising an interrogator for commanding the reader to communicate data from the interpretation circuit.

4. The system according to claim 1 further comprising a second color sensor for evaluating the condition of the illuminated sterilization sensor, wherein the interpretation circuit interprets the output of the first color sensor and the second color sensor to determine whether the optical change has taken place.

5. The system according to claim 1 wherein the reader has at least one tortuous path adapted for conveying gas to the sterilization sensor.

6. A method of determining the efficacy of the sterilization process, comprising the steps of:
   providing a sterilization sensor comprising an indicator that undergoes an optical change when exposed to an efficacious sterilization process;
   providing a reader, comprising:
      (a) an illumination source for illuminating the sterilization sensor,
      (b) a color sensor for evaluating the condition of the illuminated sterilization sensor, (c) an interpretation circuit for interpreting the output of the color sensor to determine whether the optical chance has taken place, and (d) a communication circuit for communicating data from the interpretation circuit to a location outside of the package;

placing the sterilization sensor within the reader, the reader adapted for inclusion within packs of goods to be sterilized and having chemical resistance capable of withstanding sterilizing conditions multiple times and through multiple uses;

placing the reader with the sterilization sensor inside a package of goods;

subjecting the package to sterilizing conditions; and interrogating the reader without opening the package to learn whether the optical change has taken place.

7. The method according to claim 6 wherein the sterilization sensor is disposable and the reader is reusable.

* * * * *

UNITED STATES PATENT AND TRADEMARK OFFICE
CERTIFICATE OF CORRECTION

PATENT NO. : 7,122,150 B2
APPLICATION NO. : 10/044441
DATED : October 17, 2006
INVENTOR(S) : Bernard A. Gonzalez It is certified that error appears in the above-identified patent and that said Letters Patent is hereby corrected as shown below:

<u>Column 1:</u>
Line 16, Delete "modem" and insert -- modern --, therefor.

<u>Column 5:</u>
Line 53, Delete "precedures" and insert -- procedures --, therefor.
Line 59, Delete "disseminateing" and insert -- disseminating --, therefor.

<u>Column 6:</u>
Line 6, Delete "electromagentic" and insert -- electromagnetic --, therefor.
Line 8, Delete "antenae" and insert -- antennae --, therefor.
Line 30, In Claim 1, after "comprising" insert -- : --.

<u>Column 7:</u>
Line 3, In Claim 6, delete "chance" and insert -- change --, therefor.

Signed and Sealed this

Fourteenth Day of August, 2007

JON W. DUDAS
*Director of the United States Patent and Trademark Office*